United States Patent [19]

Junker et al.

[11] Patent Number: 5,666,051

[45] Date of Patent: Sep. 9, 1997

[54] SYSTEM AND METHOD FOR MAPPING RESIDUAL SURFACE STRESSES IN A VALUE RING

[75] Inventors: Warren R. Junker, Monroeville; Lee W. Burtner, Elizabeth Twp., Allegheny County; Michael G. Peck; Richard J. Makar, both of Greensburg; David A. Chizmar, Export, all of Pa.

[73] Assignee: Thermo King Corporation, Minneapolis, Minn.

[21] Appl. No.: 539,241

[22] Filed: Oct. 4, 1995

[51] Int. Cl.$^6$ .......................... G01R 33/12; G01N 27/72; G01B 7/24
[52] U.S. Cl. .......................... 324/209; 324/225; 324/234; 324/238
[58] Field of Search ........................... 324/209, 262, 324/236–243, 225

[56] References Cited

U.S. PATENT DOCUMENTS 4,528,856  7/1985  Junker et al. .
4,755,753  7/1988  Chern .................................. 324/237
5,394,083  2/1995  Jiles .................................... 324/226

Primary Examiner—Walter E. Snow

[57] ABSTRACT

Both a system and method are provided for mapping the magnitude of residual compressive stresses over the surface of a ferromagnetic machine component, such as a valve ring of the type used in refrigeration compressors. The system includes an eddy current probe having a detection coil for emanating a fluctuating electromagnetic field that shallowly penetrates the surface of the valve ring or other ferromagnetic component, a probe circuit connected to the coil for both conducting a high frequency alternating electric current through the coil and detecting changes in the impedance in the coil, and a scanning mechanism having a turntable for supporting and rotating the component. A support arm positions the coil of the eddy current over a central portion of the valve ring while the ring is rotated by the turntable and changes in coil impedance are detected by the probe circuit. A microprocessor converts the fluctuations in the impedance detected by the eddy current probe circuit into residual stress values, and correlates these values with regular positions on the valve ring in order to generate a map of the residual surface stresses over the ring.

17 Claims, 2 Drawing Sheets

SYSTEM AND METHOD FOR MAPPING RESIDUAL SURFACE STRESSES IN A VALUE RING

BACKGROUND OF THE INVENTION

This invention generally relates to a system and method for mapping the magnitude of residual surface stresses of a machine component, and is particularly concerned with the mapping of residual compressive surface stresses of a ferromagnetic valve ring with an eddy current probe in order to assure the fatigue life of the ring.

Suction ring valves are critical components of compressors used in refrigeration units. As such, they have to be extremely reliable. The service life of compressor valve depends upon its resistance to fatigue. To maximize the fatigue life of such rings, the manufacturers (after die cutting and heat treating the rings) tumble them in order to induce surface compressive stresses.

Ideally, a finished valve ring should be free of superficial defects, having a good surface finish, have good flatness and round edges, and most importantly should have a uniform high compressive residual stress of at least 70 ksi at all points on its surface in order to maximize the fatigue strength and hence durability of the valve ring. However, flatness requirements sometime requires the valve manufacturer to straighten the ring after tumbling. In such a straightening operation, the ring is essentially bent along one of its diameters in order to counteract an unwanted mount of camber or curl in the ring. Unfortunately, such a bending of the ring can reduce or neutralize completely the compressive stresses present in the surface of the ring along the diameter where it is bent, thereby substantially shortening its fatigue life. Worse yet, such bending can introduce tensile stresses along the bending diameter which can shorten the fatigue life of the ring even more. Consequently, such straightened valve rings will tend to prematurely crack along the diameter where they were bent in order to counteract the unwanted camber or curl that they were initially manufactured with. When such cracking occurs, the operation of the refrigeration compressor that such rings are used in fails.

While x-ray diffraction techniques are known which are capable of mapping the pattern of compressive stresses that exist around the circumference of such ring-shaped components, such techniques are slow and expensive to implement. Thus they are not well suited for the rapid inspection of a batch of 100 or 1000 compressor rings.

Clearly, there is a need for a system for mapping the residual surface stresses present in ferromagnetic components such as valve rings that is quicker, easier, and more reliable than prior art x-ray diffraction techniques. Ideally, such a system should be capable of quickly and reliably inspecting hundreds or thousands of such valve rings so that rings with inadequate compressive surface stresses may be discarded before being assembled into refrigeration compressors.

SUMMARY OF THE INVENTION

Generally speaking, the invention is both a system and method for mapping the magnitude of residual surface stresses over the surface of a metallic component, such as a ferromagnetic valve ring used in a refrigeration compressor. The system comprises an eddy current probe having a detection coil for emanating a fluctuating electromagnetic field that penetrates little beyond the surface of the ferromagnetic component, and a probe circuit connected to the coil for both conducting a fluctuating electric current through the coil and detecting changes in the impedance thereof. The system further includes a scanning mechanism for scanning the detection mechanism over a central portion of the surface of the metallic component while changes in coil impedance are detected by the probe circuit, as well as a microprocessor electrically connected to both the scanning mechanism and the probe circuit for converting the changes of impedance into a map of the magnitude of residual surface stresses over at least a portion of the component.

The maximum width of the detection coil of the eddy current probe is substantially smaller than the width of the metallic component scanned in order to avoid interaction between the fluctuating magnetic field and the edges of the component. In the preferred embodiment, the maximum width of the detection coil is less than 5% of the width of the portion of the component being mapped.

Additionally, the probe circuit of the eddy current probe conducts an alternating electric current through the coil of a frequency sufficiently high so that the resulting electromagnetic field penetrates no more than 0.10 millimeter beyond the surface of the component, and preferably no more than 0.025 millimeters. In the preferred embodiment, the frequency of the alternating electric current is between 0.5 and 4 megahertz, and most preferably 2 megahertz.

The system is particularly well adapted for mapping the residual compressive stresses in annular components such as the valve rings used in refrigeration compressors. To this end, the scanning mechanism includes a support arm for holding the relatively small-diametered coil of the eddy current probe, and a turntable for both supporting and rotating the annular component. During the operation of the scanning mechanism, the support arm supports the coil of the eddy current probe in a central portion of the annular component to avoid unwanted interactions between the magnetic field emanated by the coil with the edges of the component. Additionally, the scanning mechanism includes a motor for rotating the turntable, as well as an encoder for generating a signal pulses indicative of the degree of revolution of the turntable. A switch controls the input of electrical power into the turntable motor, and the encoder and the switch are connected to the microprocessor of the system so that the microprocessor can switch the turntable motor off after it has turned the annular component at least one revolution.

In the method of the invention, an annular component such as a valve ring is placed onto the turntable of the scanning mechanism. Next, the support arm is positioned so that the coil of the eddy current probe engages a central portion of the annular component. The microprocessor then simultaneously actuates the probe circuit and the turntable of the scanning mechanism. The impedances detected by the eddy current probe circuit as a 1 Mhz current is conducted through the coil is fed into the microprocessor, along with the signal pulses generated by the encoder connected to the turntable. The microprocessor then generates a map of residual stresses of the annular component by converting the detected impedances into residual stress values and correlating these stress values with the angular position of the component with respect to the probe coil.

The system and method provide a simple, quick and reliable means for determining the pattern of residual surface stresses 360° around a central portion of the compressor ring or other annular metallic component.

BRIEF DESCRIPTION OF THE SEVERAL FIGURES

FIG. 3 is a plan view of a valve ring of the type that the system of the invention is designed to map the residual surfaces stresses of.

DETAILED DESCRIPTION OF THE PREFERRED EMBODIMENT

Figure 1:
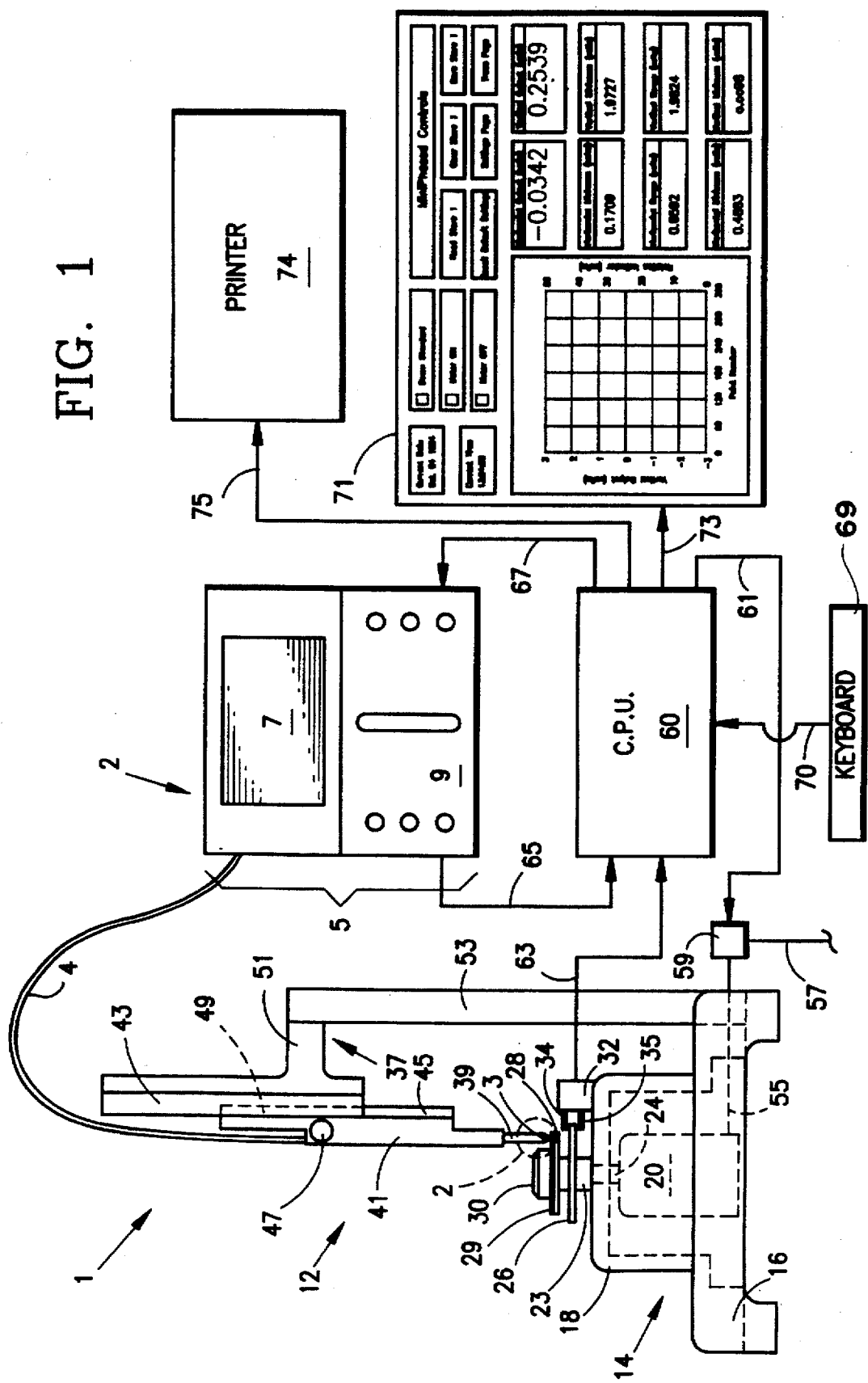
FIG. 1 is a schematic view of the mapping system of the invention that includes a side view of the scanning mechanism used in the system.
Figure 2:
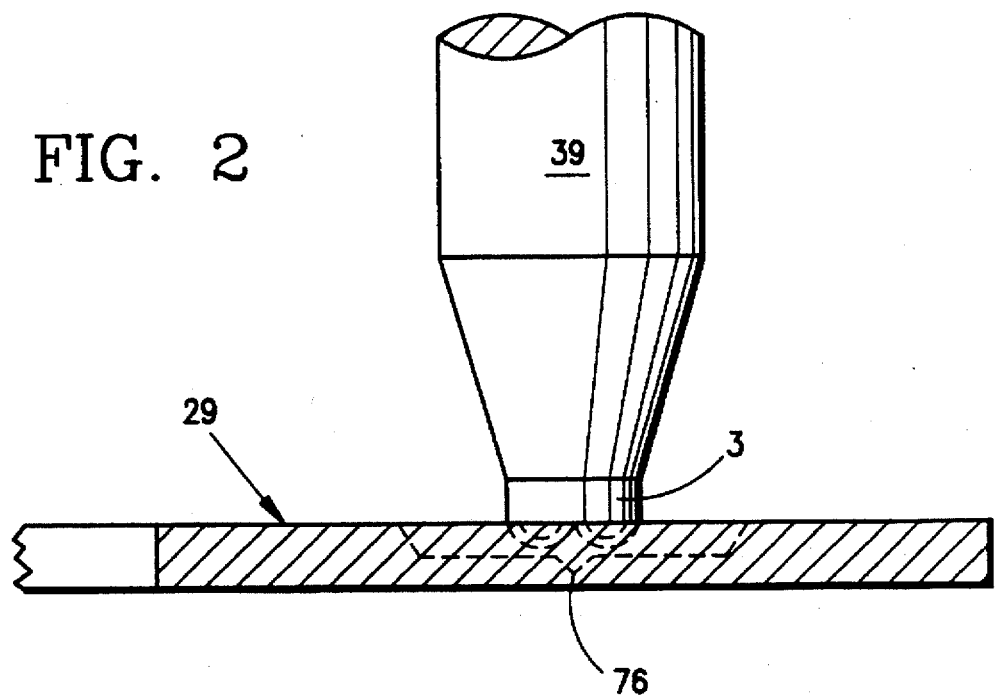
FIG. 2 is an enlargement of the distal end of the stylus of the scanning mechanism, illustrating how it engages the detection coil of the eddy current probe against a midportion of a valve ring.

With reference now to FIGS. 1 and 2, wherein like figures designate like components throughout all the several figures, the system 1 of the invention generally comprises an eddy current probe 2 in combination with a ring scanning mechanism 12, probe support assembly 37, a microprocessor 60, a mapping display monitor 71, and a printer 74.

The eddy current probe 2 includes a detection coil 3 that is connected by way of a flexible cable 4 to a probe circuit assembly 5. In the preferred embodiment, the detection coil 3 is a Hocking model 125-2M probe coil available from Kraut, Kramer, & Branson, Inc., located in Lewistown, Pa. Such a coil is only 0.04 inches in diameter which, as is illustrated in FIG. 2, allows the fluctuating magnetic field emanated thereby to be confined to a central portion 76 of the ring 29 (or other workpiece) well away from the edges of the ring 29. With specific reference again to FIG. 1, the probe circuit assembly 5 includes a menu screen 7 for displaying the various operating options of the probe 2, and a multi-frequency generator 9. The generator 9 not only generates the alternating current that is conducted through the coil 2 via cable 4; it further measures the impedance of the coil 3 with respect to the alternating current as the coil 3 is scanned around a middle portion 76 of a valve ring 29 or other workpiece. In the preferred embodiment, both the menu screen 7 and the multi-frequency generator 9 are part of a Hocking model eddy current probe again available from Kraut, Kramer & Branson, Inc. In instances where the valve ring 29 or other workpiece is formed from a ferromagnetic material, the impedance of the coil 3 is indicative of the magnitude of compressive stresses in the surface of the ring 29. While the multi-frequency generator 9 can generate alternating current over a broad frequency range, a frequency range of between 1 to 3 megahertz is preferred in order to maintain the lines of flux of the alternating magnetic field emanated by the probe 3 close to the surface of the ring 29 (i.e., only 0.025 mm penetration through the ring surface).

With reference again to FIG. 1, the scanning mechanism 12 of the system 1 generates a relative movement between the ring 29 or other workpiece and the detection coil 3 so that variations in the coil impedance (which correspond to variations and residual surface stresses) may be mapped along a central portion of the ring 29. To this end, the scanning mechanism 12 includes a turntable assembly 14. The assembly 14 is formed from a base 16 that supports a motor housing 18 containing an electric motor 20. The motor 20 preferably includes an internal transmission (not shown) that causes its output shaft 24 to turn at approximately 10 rpms. The electric motor 20 drives a turntable 22 having a shaft 23 that is rotatably mounted in the top wall of the motor housing 18. Turntable shaft 23 is coupled to motor shaft 24 as indicated. The turntable shaft 23 includes, on its lower portion, an optical disc 26 having a plurality of uniformly spaced teeth (not shown) around its periphery for a purpose that will be explained presently. The turntable shaft 23 further includes, at its upper end, a ring support platform 28 for supporting an annular valve ring 29. A screw cap 30 is included at the distal end of the turntable shaft 23 in order to secure the valve ring 29 in place over the platform 28. Located on top of the motor housing 18 adjacent to the optical disc 26 is an optical encoder 32. Encoder 32 includes a light emitter 34 spaced apart from a photosensor 35. The teeth located around the periphery of the optical disc 26 alternately conduct and interrupt the beam of light transmitted between the emitter 34 and photosensor 35, and the rotational position and speed of the turntable 22 may be inferred from the resulting voltage pulses generated by the photosensor 35.

The probe support assembly 37 secures the detection coil 3 of the eddy current probe 2 in wiping engagement with a central portion 76 of a valve ring 29 or other workpiece. The previously mentioned stylus 39 of the probe support assembly 37 is connected to a vertically adjustable member 41 that is slidably connected to a stationary, vertical support member 43 by means of a dovetail joint 45. An adjustment knob 47 is connected to a gear wheel (not shown) that engages the teeth of a rack 49. The manual turning of the knob 17 allows the vertically adjustable member 41 to move the stylus 39 up or down in microscope-type fashion. The vertical support member 43 is in mm supported by an arm 51 connected to a column 53 mounted in the base 16 of the turntable assembly 14. Finally, a motor power cord 55 extends out of the base 16 of the turntable assembly 14, where it is connected to a 110 volt power source 57 by way of a switching circuit 59. In the preferred embodiment, switching circuit 59 may be any one of a number of commercially available triacs capable of conducting or shutting off a 110 volt power source upon the receipt of a control signal of 5 volts or less of the type typically generated by TTL circuitry.

The system 1 further includes a microprocessor 60 for coordinating and controlling the operation of the multi-frequency generator 9 of the eddy current probe 2, and the scanning mechanism 12. In the preferred embodiment, the microprocessor 60 is a Model No. 486-66 microcomputer having a Metrobyte DAS-802 converter board manufactured by Gateway 2000 located in North Sioux City, S.D. A cable 61 connects the output of the microprocessor 60 to the switching circuit 59 so that the microprocessor 60 can actuate or de-actuate the electric motor 20 of the turntable assembly 14. Additionally, a cable 63 conducts the output of the encoder 32 to the input of the microprocessor 60 so that the microprocessor can compute, from the signal pulses generated by the previously-described photosensor 35, the angular position of the shaft 23 and hence of a valve ring 29 secured onto the ring support platform 28. Another cable 65 connects the impedance output of the multi-frequency generator 9 of the eddy current probe 2 to the input of the microprocessor 60 so that the microprocessor 60 may infer the residual surface stresses of the valve ring 29 by associating these impedance signals with surface stresses via a preprogrammed look-up table. Another cable 67 connects the output of the microprocessor 60 to the multi-frequency generator 9 of the eddy current probe 2 so that the microprocessor 60 may actuate or de-actuate the multi-frequency generator 9. A keyboard 69 is connected to the input of the microprocessor 60 via a cable 70, while a mapping display monitor 71 is connected to an output of the microprocessor 60 via another cable 73. A printer 74 is further connected to the output of the microprocessor 60 via a cable 75 so that the microprocessor might make a permanent record of the surface stresses present in a particular valve ring 29 scanned by the detection coil 3. The printer 74 is preferably a Desk Jet Model No. 520 (or manufactured by Hewlett Packard), although any one of a number of different models of commercially available printers will suffice.

The method of the invention parallels the operation of the previously-described system 1. In the first step of this method, a valve ring 29 having an acceptable surface stress pattern (i.e., surface stresses of at least 70 ksi over all points) is first mounted in the turntable assembly 14 of the scanning mechanism 12 by means of securing cap 30. Next, the height of the detection coil 3 is adjusted via knob 47 of the probe support assembly 37 so that the coil 3 very slightly wipingly engages a central portion of the annularly shaped valve ring 29. The microprocessor 60 is then actuated, which in turn actuates the probe circuit assembly 5, the mapping display monitor 71 and the printer 74. The operator of the system 1 types in a "start scan" command to the microprocessor 60 via keyboard 70, and the microprocessor 70 transmits a signal to the switching circuit 59 that doses it, thereby actuating turntable shaft 20. Simultaneously, frequency generator 9 of the eddy current probe 2 transmits an alternating current through the detection coil 3 of approximately 2 megahertz so that the resulting, fluctuating electromagnetic field emanating from the probe coil 2 penetrates the surface of the valve ring 20 or other workpiece to a depth of only about 0.025 millimeters. As the valve ring 29 is rotated, the optical encoder 32 generates pulses that the microprocessor 60 can translate into angular positions on the ring 29 by means of a preprogrammed look-up table. The surface stresses computed by the microprocessor 60 are associated with the angular positions inferred from the pulses received by the optical encoder 32 and integrated into a graph displayed by the mapping display monitor 71. After the microprocessor 60 has determined that the ring 29 has been turned at least 360°, it de-actuates the motor 20 by opening the switching circuit 59, and further shuts down the multi-frequency generator 9 of the eddy current probe 2. The system operator then checks the graph displayed by the mapping display monitor 71, and compares it with the premeasured, surface stress values associated with the calibration ring 29. If these values match, the system operator again tests the initial accuracy of the system 1 by scanning a second calibration ring known to have an unacceptable distribution of surface stresses (i.e., surface stresses less than 70 ksi on one or more portions). If the resulting surface stress map generated by the display monitor 71 conforms to the premeasured surface stress value of the second calibration ring, then the system operator concludes that the system 1 is properly calibrated, and proceeds to measure the surface stresses of a batch of valve rings or other components whose surface stresses are unknown. If, on the other hand, the system 1 fails either of these two calibration tests, the system operator adjusts either or both of the position of the detection coil 3 via the probe support assembly 37 or the settings of the probe circuit assembly 5 until the stress maps generated by the system 1 conform to the known stress patterns existing in the two calibration rings.

Once the system 1 has been calibrated, the operator then proceeds to map the residual stress patterns of a batch of valve rings or other workpieces. After the mapping operation has been completed and displayed on the mapping display monitor 71, the microprocessor 60 commands the printer 74 to print the map displayed on the monitor 71. Of course, the microprocessor 60 is preferably operated in conjunction with software that records such data as a particular batch number that the valve ring belongs to, the date of the test, the frequency of the alternating current conducted through the detection coil 3, etc. In the case of valve rings, the microprocessor 60 is programmed to indicate that the ring "passed" the mapping test if the coil impedances monitored by the multi-frequency generator 9 indicate that a stress magnitude of at least 70 ksi is present on all portions of the ring surface tested. By the same token, microprocessor 60 is programmed to indicate that a particular ring failed a mapping test if the impedances monitored indicate that residual surface stresses of less than 70 ksi at any point along the 360° path monitored by the detection probe 3. After every one of the batch of fings 29 has been scanned, the previously-mentioned calibration step is repeated to insure the integrity of the stress distribution maps obtained.

Figure 3:
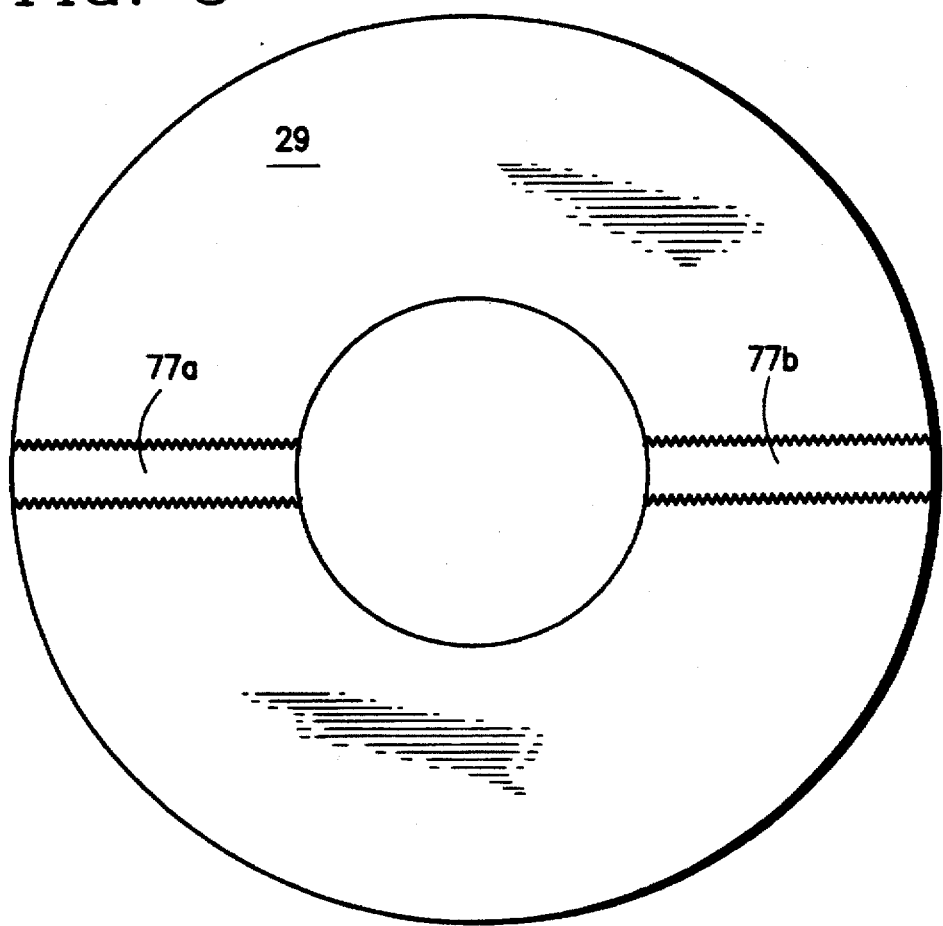

Typically, in the case of a failed ring (as may best be understood with respect to FIG. 3), the system 1 will detect two radially oriented areas 77a,b of sub 70 ksi residual surface stresses that are disposed 180° from one another. As was mentioned previously in the Background section, such a pattern results from a manufacturer's attempt to straighten a curled valve ring by bending it in a direction opposite to that of an unwanted curl. Such bending applies shear stresses in the ring 29 along the line of the bend which either reduce or neutralize completely the residual compressive stresses deliberately generated on the surface of the ring 29 by either a tumbling or a cleaning process.

The instant invention provides an eddy current based system that is often two or three times as sensitive to variations in the residual compressive stresses in a ferromagnetic workpiece than systems based on x-ray diffraction with components that cost about one-fiftieth as much as the components of an x-ray diffraction device. Moreover, the eddy current based scanning procedure of the invention takes only a fraction of the time that x-ray diffraction takes.

While the operation of the system has been described with respect to the mapping of residual surface stresses and valve rings, it may in fact be used to map the residual surface stresses of any component formed from a ferromagnetic material.

What is claimed:

1. A system for mapping the magnitude of residual surface stresses over a surface of an annular metallic component, comprising:

an eddy current probe having a detection coil for emanating a fluctuating electromagnetic field that focuses primarily on the surface of the metallic component, wherein the maximum width of the detection coil is substantially smaller than the radial width of the metallic component scanned to avoid interaction between said fluctuating magnetic field and edges of said component, and a probe circuit connected to said coil for both conducting a fluctuating electric current through said coil and detecting changes in the impedance of the coil;

means for scanning said detection coil over the surface of said annular metallic component in a 360° path around a central annular portion of said component while monitoring changes in coil impedance detected by said probe circuit, including a turntable means for rotating said annular metallic component, and a support arm for positioning said detection coil against the surface of the annular metallic component while said component rotates, and processor means electrically connected to said scanning means and said probe circuit for converting said changes in impedance into signals generating a map of the magnitude of residual surface stresses around a central portion of the surface of the annular component.

2. The system defined in claim 1, wherein the frequency of the fluctuating electric current conducted through the detection coil of the probe is sufficiently high so that the resulting fluctuating magnetic field penetrates no more than about 0.1 millimeter beyond the surface of the component.

3. The system defined in claim 1, wherein the frequency of the fluctuating electric current through the coil of the eddy current probe results in a fluctuating magnetic field that penetrates no more than about 0.025 millimeters beyond the surface of the metallic component.

4. The system defined in claim 2, wherein the frequency of the electric current conducted through the coil of the eddy current probe is between 0.5 and 4 megahertz.

5. The system defined in claim 1, wherein the maximum width of the detection coil is less than 25% of the width of the metallic component scanned.

6. The system defined in claim 1, wherein said scanning means includes a means for generating a signal indicative of the amount of angular movement of said metallic component by said turntable means, and a switch means for actuating and actuating and deactuating said turntable means.

7. A system as defined in claim 6, wherein said processor means is electrically connected to said signal generating means and to said switch means and operates to de-actuate said turntable means after a selected amount of angular movement.

8. A system as defined in claim 1, wherein said component is a flat annular ring having a width along its radius, and wherein said support arm positions said coil over a central portion of said radial width of said ring.

9. A system for mapping the magnitude of residual compressive surface stresses over a surface of an annular ferromagnetic component, comprising:

an eddy current probe having a detection coil for emanating a fluctuating electromagnetic field that penetrates no more than about 0.10 millimeters beyond the surface of the component, wherein the maximum width of the detection coil is no more than about 20% of the width of the ferromagnetic component scanned to avoid interaction between said fluctuating magnetic field and edges of said component, and a probe circuit connected to said coil for both conducting a fluctuating electric current through said coil and detecting changes in the impedance of the coil;

means for scanning said detection coil over the surface of said annular metallic component in a 360° path around a central annular portion of said component while monitoring changes in coil impedance detected by said probe circuit, including a turntable means for rotating said annular metallic component, and a support arm for positioning said detection coil against the surface of the annular metallic component while said component rotates, and processor means electrically connected to said scanning means and said probe circuit for converting said changes in impedance into signals generating a map of the magnitude of radially oriented residual surface stresses over said central annular portion of the surface of the component.

10. A system defined in claim 9, wherein the frequency of the fluctuating electric current conducted through the detection coil of the probe is sufficiently high so that the resulting fluctuating magnetic field penetrates no more than about 0.025 millimeters beyond the surface of the ferromagnetic component.

11. The system defined in claim 9, wherein the frequency of the fluctuating electric current conducted through the coil of the eddy current probe is about 1 megahertz.

12. The system defined in claim 9, wherein said scanning means includes means for generating signal pulses indicative of the mount of angular movement of said ferromagnetic component by said turntable means, and a switch means for actuating and deactuating said turntable means.

13. The system as defined in claim 12 wherein said processor means is electrically connected to said signal generating means and said switch means and operates to de-actuate said turntable means after a selected number of rotations.

14. A system as defined in claim 1, wherein the ferromagnetic component is a flat annular ring having a width along its radius, and wherein the support arm positions the coil over a central portion of the radial width of the ring.

15. The system as defined in claim 9, further including at least one calibration component for calibrating said eddy current probe.

16. The system as defined in claim 12, wherein said turntable means functions to rotate said ferromagnetic component at a speed of at least 10 rpms.

17. A method for mapping the magnitude of radially oriented residual surface stresses over a surface of an annular metallic component by means of an eddy current probe having a detection coil for emanating a fluctuating electromagnetic field that penetrates little beyond the surface of the metallic component, the maximum width of said probe coil being substantially smaller than the radial width of the annular component, a probe circuit connected to said coil for both conducting a fluctuating electric current through said coil and detecting changes in the impedance of said coil, and a turntable means for rotating said annular metallic component comprising the steps of:

rotating said annular metallic component with said turntable means while annularly scanning said detection coil in a 360° path around a central annular portion of said annular metallic component;

detecting changes in the impedance of the coil while said coil scans said component;

converting said detected changes in impedance to changes in the surface stresses of the component, and correlating said changes in said surface stresses to locations on the component to map said surface stresses on at least a portion of said component.

* * * * *